United States Patent [19]

Anderson et al.

[11] Patent Number: 5,087,573
[45] Date of Patent: Feb. 11, 1992

[54] MONOCLONAL ANTIBODY AGAINST BONE ALKALINE PHOSPHATASE

[75] Inventors: H. Clarke Anderson, Shawnee Mission, Kans.; Kensaku Masuhara, Kobe, Japan

[73] Assignee: University of Kansas, Kansas City, Kans.

[21] Appl. No.: 162,995

[22] Filed: Mar. 2, 1988

[51] Int. Cl.$^5$ .................. C12N 5/20; C07K 15/28
[52] U.S. Cl. ....................... 435/240.27; 530/387
[58] Field of Search ............... 530/387; 435/240.27

[56] References Cited

PUBLICATIONS

Craig S. Hill and Robert L. Wolfert, Clin. Chem. Acta 186: 315–320 (1989).
Singh, I. and K. Y. Tsang, Expt'l Cell Res. 95:347–358 (1975).
C. S. Hill (1990) Bone Min. Res. 5 (Suppl 2) S 175, No. 395.
Alfred J. Crowle, *Immunodiffusion*, Academic Press, 1961, pp. 11–18 and 68–69.
Feinberg, J. G., Int. Arch. Allergy 11:129–152 (1957) pp. 129–130, 143–145.
Darcy, P. A., Clin. Chim. Acta. 38:329–337 (1972) pp. 329–332.
Zola, Heddy, *Monoclonal Antibodies: A Manual of Techniques*, CRC Press, 1987, pp. 6 and 50.
McComb, R. B. et al. (1979) *Alkaline Phosphatase*, Plenum Press, New York, p. 50.
Weiss et al., Proc. Natl. Acad. Sci. 83: 7182–7186 (1986).
Meyer et al., Clin. Chim. Acta 126: 109–117 (1982).
Lawson et al., Clin. Chem. 31/3: 381–385 (1985).
Nair et al., Arch. Biochem. Biophys. 254:18–27, 1987.
Bailyes et al., Biochem. J. 244:725–733, 1987.
Kipps et al., pp. 108.1–108.9 m, Weir et al. Ed., Handbook of Exptl. Immunology, vol. 4, Blackwell Sci. Publ., 1986.

*Primary Examiner*—Robert J. Warden
*Assistant Examiner*—Paula Hutzell
*Attorney, Agent, or Firm*—Felfe & Lynch

[57] ABSTRACT

Monoclonal antibody (mAb) 1E10.1 immunologically distinguishing human bone from human liver alkaline phosphatase isoenzymes by specific binding to the former and not the latter is developed. mAb 1B12 is useful as a positive control as it reacts with human bone and liver ALP. Also developed is mAb 2B11 (2B11.1) which is useful as a positive control in rat ALP systems as it reacts with rat bone, liver, kidney and cartilage ALP.

7 Claims, 5 Drawing Sheets

MONOCLONAL ANTIBODY AGAINST BONE ALKALINE PHOSPHATASE

This invention concerns monoclonal antibody selective for bone alkaline phosphatase (ALP) and therefore useful for clinical testing.

SUMMARY

Monoclonal antibodies which distinguish between bone and liver or bone and kidney ALP have been developed.

DETAILED DESCRIPTION OF THE DRAWINGS

Figure 1:
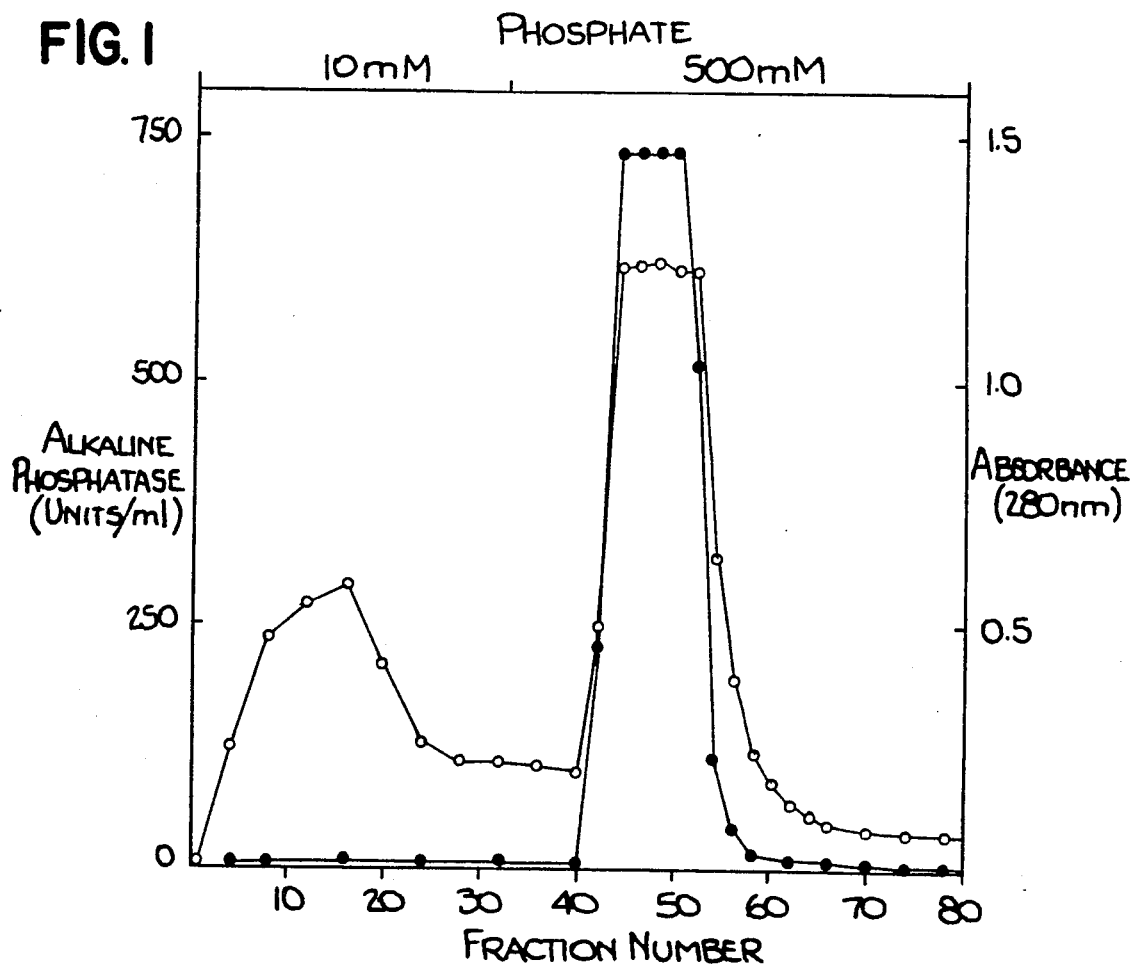
FIGS. 1-4 depict the purification steps for bone ALP showing the elution profiles from Bio Gel-HT, DEAE Sepharose CL-6B, Sephacryl S-400 and rechromatographed Sephacryl S-400 columns respectively.

FIG. 1: The resolubilized material from the second step was applied to a column (2.5 cm diam. × 8 cm long) of Bio gel-HT equilibrated with 10 mM phosphate buffer (pH 7.6)0.1 mM $MgCl_2$/0.01 mM $ZnCl_2$. The column was washed with 2 column volumes of equilibrating buffer and eluted in a stepwise manner with 150 ml of 500 mM phosphate buffer (pH 7.6)/0.1 mM $MgCl_2$/0/01 mM $ZnCl_2$ with monitoring throughout of enzyme activity (●) and protein absorbance at 280 nm (0).

Figure 2:
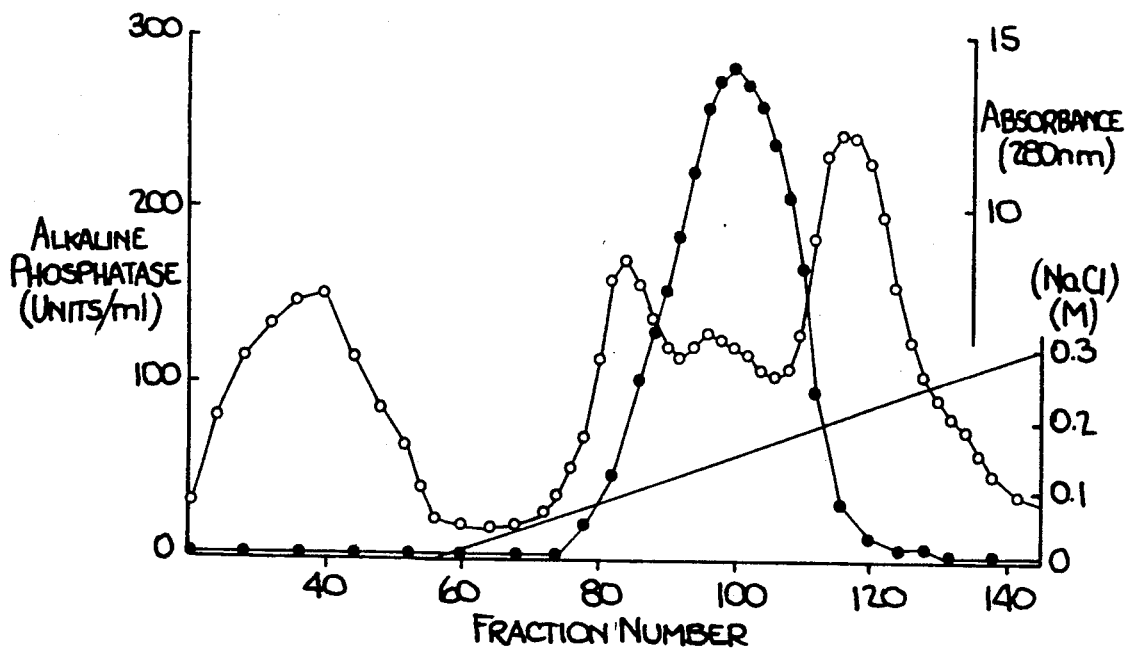

FIG. 2: The active fractions were collected and dialysed against Tris buffer. The material was applied to a DEAE Sepharose CL-6B column (2.5 cm diam. ×cm long) equilibrated with Tris Buffer and eluted with 320 mL Tris buffer that contained NaCl in a linear gradient 0 to 0.4M at a flow rate of 25 ml/h. Elution profile of alkaline phosphatase from DEAE Sepharose CL-6B. Enzyme activity (●) and protein (absorbance at 280 nm; 0) were monitored throughout a stepwise gradient of NaCl from 0 to 0 4M in Tris buffer (pH 8.0)/0.1 mM $MgCl_2$/0.01 mM $ZnCl_2$. The linear gradient was started after a buffer wash (two column volumes) after sample application.

Figure 3:
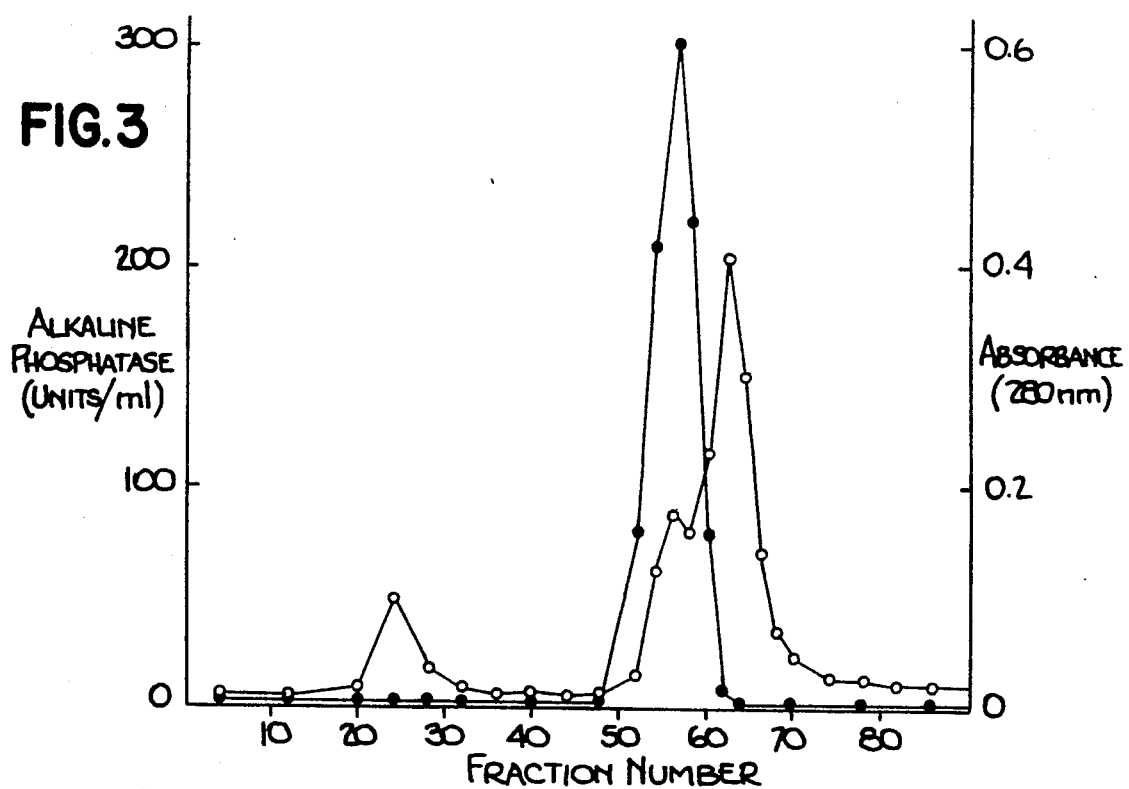

FIG. 3: Gel filtration of alkaline phosphatase on Sephacryl S-400. Enzyme activity (●) and protein (absorbance at 280 nm; 0) were monitored during elution of the proteins with 25 mM Tris buffer (pH 8.0)/100 mM NaCl/0.1 mM $MgCl_2$/0.01 mM $ZnCl_2$) from a column of Sephacryl S-40 equilibrated with the same buffer. Fractions corresponding to the activity peak eluted at about 0.15M NaCl were pooled and dialysed against a solution of $NH_4OH$ (pH 8.00)/0.1 mM $McCl_2$/0.01 mM $ZnCl_2$. The material was lyophilysed and dissolved in Tris buffer, containing 0.1M NaCl.

Figure 4:
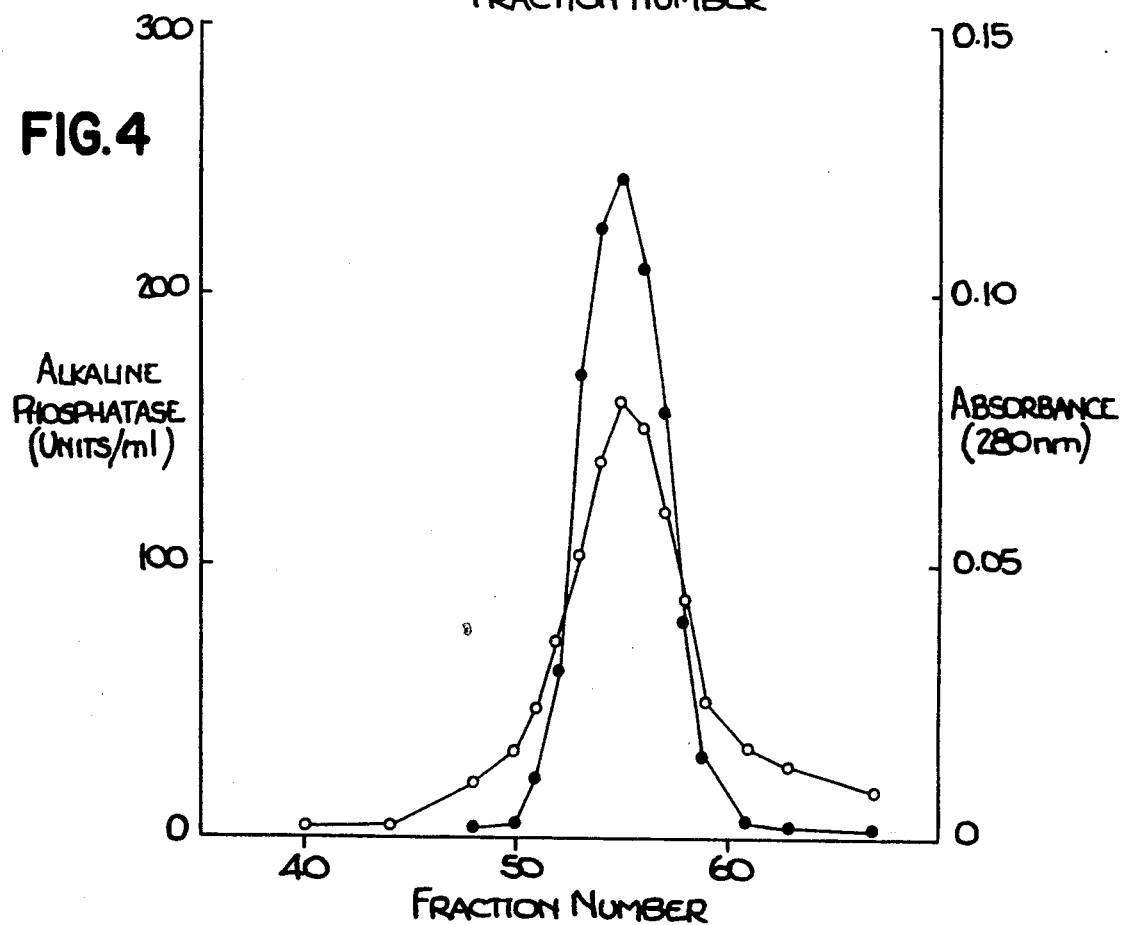

FIG. 4: The active fractions from the Sephacryl S-400 were concentrated in the same manner as for step 5 (FIG. 3) on Sephacryl S-400 and rechromatographed on the same column. Enzyme activity (●) and protein (absorbance at 280 nM); 0) were monitored during elution of the proteins under the same conditions as is described in FIG. 3.

Figure 5:
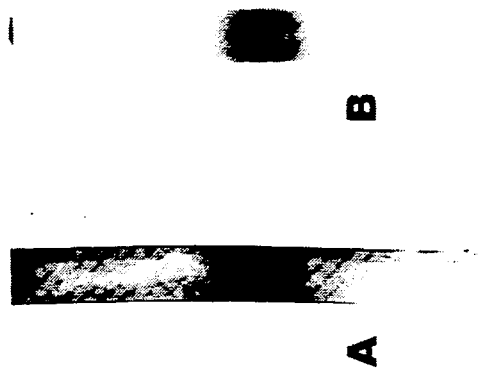

FIG. 5: This depicts the polyacrylamide gel electrophoresis of the final purified enzyme as a single protein band which was active on beta-naphthyl phosphate. Gel A was stained for alkaline phosphatase activity as described. Gel B was stained for protein with Coomassie brilliant blue 10 ug of purified enzyme was applied to each gel.

Figure 6:
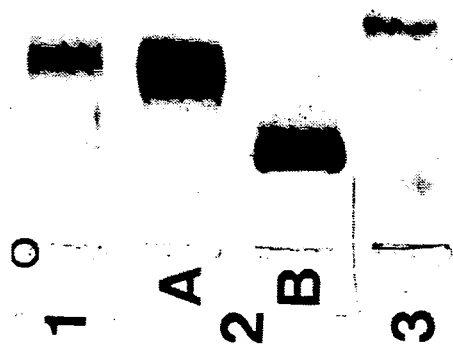
FIGS. 5-7 depict electrophoretic profiles of the purified material.

FIG. 6: This depicts electrophoretic mobility of the purified enzyme on thin-layer polyacrylamide gel before and after neuraminadase treatment. Thin-layer polyacrylamide gel electrophoresis of final purified alkaline phosphatase and standard isoenzymes. 1. Human bone alkaline phosphatase. 2A and B. Purified enzyme before and after neuraminidase treatment. 3. Human liver alkaline phosphatase. The anodal direction is from the origin (left) to the front (right). '0' indicates origin.

Figure 7:
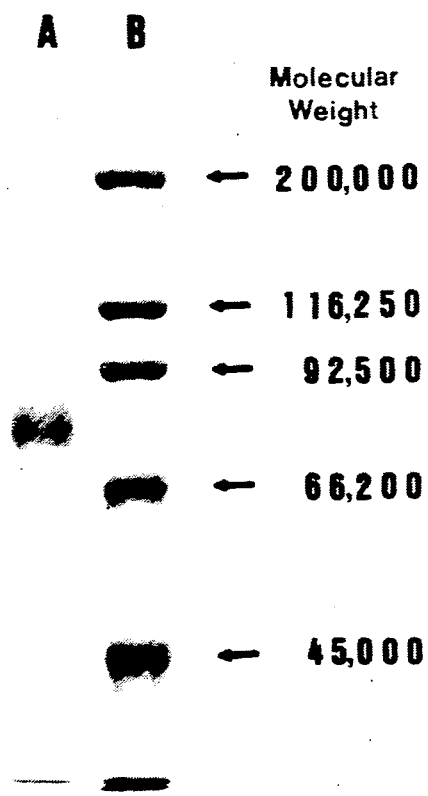

FIG. 7: This depicts SDS polyacrylamide gel electrophoresis of the final purified enzyme for molecular weight of about 80,000 daltons. SDS/polyacrylamide gel electrophoresis of final purified alkaline phosphatase (A) and marker proteins (B). The marker proteins in the kit were myosin (molecular weight 200,000), beta-galactosidase (116,250), phosphorylase B (92 500), bovine serum albumin (66 200) and ovalbumin (45 000). 15 ug of protein was applied.

Figure 8:
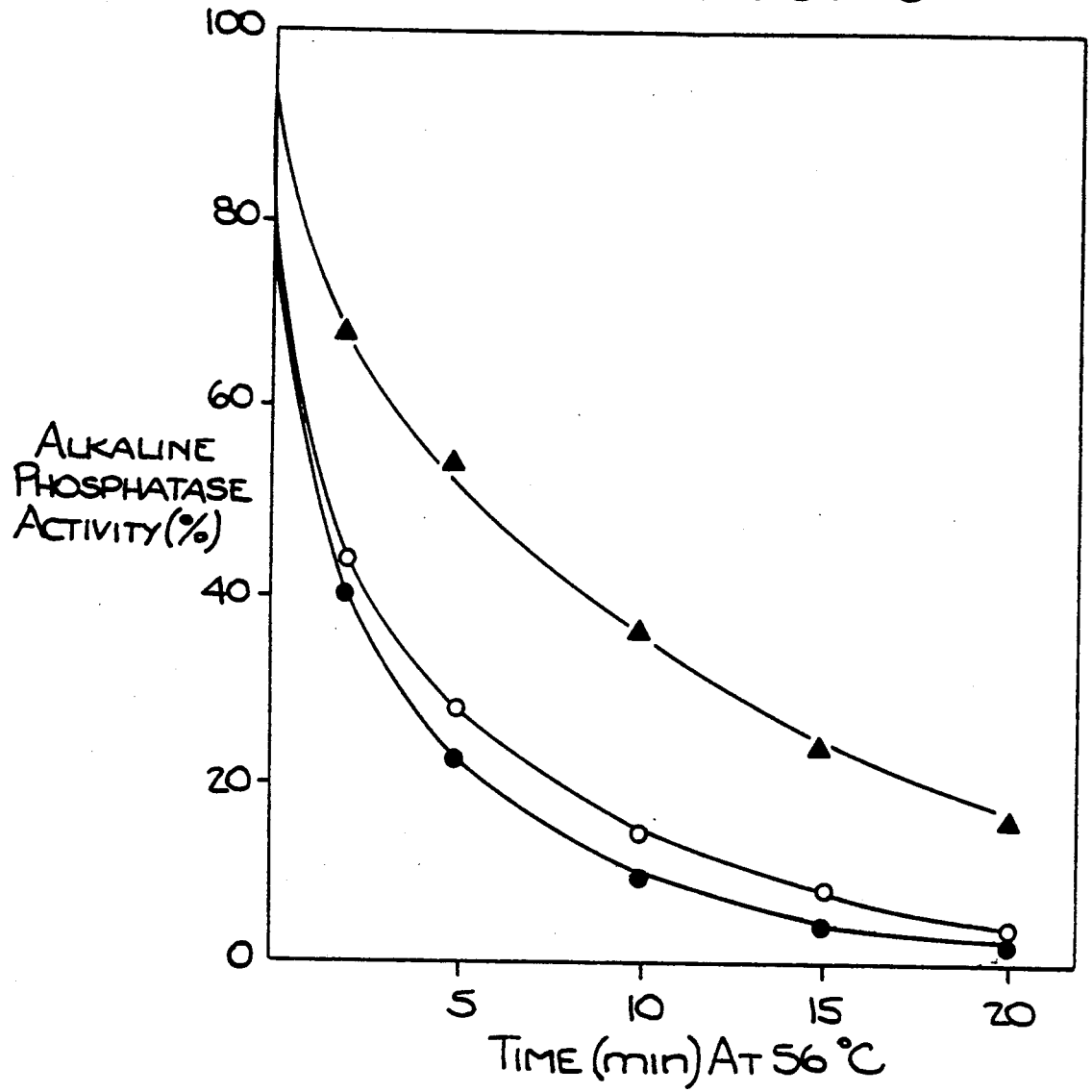
FIG. 8 summarizes results of ALP activity.

FIG. 8: This is a study on sensitivity of purified ALP to heat inactivation and inhibitions by L-homoarginine and L-phenylalanine. The heat inactivation curve of purified alkaline phosphatase and standard isoenzymes at 56° C. is shown. Measurements of residual activity of purified enzyme (0), bone isoenzyme (●) and liver isoenzyme (Δ) were made at 2, 5, 10, 15 and 20 min after the start of incubation.

DESCRIPTION

A clinical problem has persisted for years to determine whether elevated serum levels of alkaline phosphatase (ALP) in patients was due primarily to liver disease (as may occur in hepatitis or cirrhosis) or bone disease (as may occur with tumor metastatic to bone or primary osteosarcoma). It was Robison among others [Robison, R., (1923) Biochem. J. 17:286 and Franseen, C. C. and McLean, R. (1935) Am. J. Cancer 24:299]who observed that increased ALP activity was associated with bone disease. A basic problem resides in the fact that bone, liver and kidney ALP isozymes are constructed of the same or a very similar protein core; thus the two enzymes are chemically very difficult to distinguish. Antibodies to human bone, liver, or kidney isoenzymes have shown considerable cross-reactivity [Boyer, S. H. (1963) 103:938, Lehmann, F. G. (1980) Biochem. Biophys. Acta. 616:41-59]. Indeed many in the art proposed that the bone, liver and kidney ALP were the same as opposed to that from intestine and placenta (McKenna, M. J., et al. (1979) Biochem. J. 181:67-73); and our recent work using a monoclonal antibody against bovine bone ALP shows cross reaction with placenta and kidney ALP. [Oppliger, H. K., et al. (1986) Bone 7:373-378]. Clearly, the differential identification of ALP isozymes for diagnostic purposes needs a more quantitative approach [Moss, D. W. (1983) Cell Biochem. 4:70 and Lum, G. et al. (1983) Am. J. Clin. Pathol. 80:682].

The determination and/or detection of the various isozymes of ALP in biological fluids especially in blood serum is important in the diagnosis and treatment of various physical disease states. Such determination is important for example in the detection of bone and liver disease in view of the elevated levels of ALP associated with disorders such as Paget's disease, osteosarcoma, osteomalacia, jaundice, hepatitis and the like. An early and rapid detection of elevated levels can then lead to early treatment for the disease.

Attempts to utilize the bone isoenzyme as a diagnostic marker for osteosarcoma, Paget's disease and other bone diseases has been hampered by a number of problems. Incomplete purification of the enzyme and low specific activity after purification have prevented complete characterization of bone ALP including the determination of its primary structure until recently (Weiss, M. J. et al. (1986) Proc. Natl. Acad. Sci. 83:7182).

In the past, distinction between bone ALP and liver ALP has been made in the clinical lab based upon the greater heat sensitivity of the bone isoenzyme, but this is not totally satisfactory because it is a qualitative rather than quantitative assessment (Moss, D. W. and Whitby, L. G. (1975) Clin. Chem. Acta 61:63). Recently it has been shown that bone ALP can be precipitated and separated by wheat germ lectin which phenomenon could serve as a basis for separating the two enzymes in lab testing, but there is disagreement as to whether this precipitation method is reliably quantitative [Behr, W., Barnett, J. (1986) Clin. Chem. 32:1960 and Rosalki, S. B. and Ying Foo, A. (1984) Clin. Chem. 30:1182–1186].

Our laboratory has produced a highly purified sample of bone ALP with high specific activity (Masuhara, Kensaku, et al. (1987) Bone and Mineral (3:159–170). This material was used as one of the immunogens to produce the hybridomas of the invention.

The work of Lawson et al. in (1985) Clin. Chem. 31 (3), 381–385, reports one monoclonal antibody that reacts preferentially with liver ALP, with some further cross reaction to bone, placental and intestinal ALP; which appears to be the subject of a patent application DE 3420926.

Our laboratory has developed monoclonal antibodies against rat cartilage/bone ALP which react specifically with human bone ALP versus human liver ALP (see table 3). Furthermore, these monoclonal antibodies can also discrimate between the ALPs of bone, cartilage and kidney (tables 1–3).

Bone ALP purification as described in Masuhara, Kensaku, et al. (1987) Bone and mineral, 3:159 as follows:

Human Osteosarcoma

The original tumor tissue was obtained from the patient at open biopsy under sterile conditions in 1980. Samples were then finely minced and transplanted into the subcutaneous tissue on the back of the male BALB/c adult nude mice (nu/nu) (Nippon Clea, Tokyo, Japan) in a pathogen free environment. The tumor was serially transmitted to the BALB/c strain of nude mice by the same method every 6–8 weeks. The tumor tissue was harvested, pooled and purified according to the following procedure. The average yield of transplanted tumor is 2 g per mouse.

Assay for Alkaline Phosphatase

The enzyme was assayed by measuring the release of p-nitrophenol from p-nitro-phenylphosphate at ambient temperature using a Gilford (model 250) recording spectrophotometer. The assay mixture (0.5 ml) contained 0.3M 2-amino-2-methyl-1-propanol, pH 10.2, 4 mM p-nitrophenylphosphate, 20 ug $MgCl_2$ and 10 ul of diluted enzyme (u=micro). The formation of p-nitrophenol was measured spectrophotometrically at 410 nm. Units represent u moles of p-nitrophenol formed per minute at 22° C.

Measurement of Protein

Protein concentration was determined by the method of Lowry et al. [(1951) J. Biol. Chem., 193:265]using bovine serum albumin as a standard. In the chromatographic steps, protein was monitored by the spectrophotometric measurement of absorbance at 280 nm. Control human bone alkaline phosphatase was obtained as a serum sample containing 1620 IU/L of enzyme activity from a patient with Paget's disease, and of human liver alkaline phosphatase as a serum sample containing 1420 IU/L from a patient with cholanigitis.

Polyacrylamide Gel Electrophoresis

Analytical disc electrophoreses were run in 7.0% gels in Tris/borate buffer, pH 9.5, by the method of Green et al. (Green, S., et al. (1972) Am. J. Clin. Pathol. 57:52–64). The gels were removed from the running tubes and stained for alkaline phosphatase activity colorimetrically by the method of Smith et al. (Smith, I. (1968) Clin. Chem. Acta. 19:499), and for protein with Coomasie brilliant blue.

The isoenzymes and purified bone alkaline phosphatase were analyzed by thin-layer horizontal electrophoresis on polyacrylamide gel (2mm thick) by the method of Higashino et al. (Higashino, K., et al. (1977) Clin. Chem. 23:1615). 1 ug of purified enzyme and 5 ul of serum samples were applied as standards of bone and liver isoenzymes.

The presence of carbohydrates in purified alkaline phosphatase was determined by neuraminidase treatment. In this procedure the enzyme was incubated for 16 hours at 37° C. with neuraminidase (10 U) and was applied to the same thin-layer polyacrylamide gel as described below.

Sodium Dodecyl Sulfate/Polyacrylamide Gel Electrophoresis

The subunit molecular weight of purified enzyme was analysed by SDS polyacrylamide gel electrophoresis by the method of Weber et al. (1972 Methods Enzymol. 26:3–27) using 7.5% acrylamide gel and 0.1M phosphate buffer (pH 7.2) containing 0.1% SDS, before and after reduction of S—S bonds of the sample by 2-beta-mercaptoethanol.

Heat Stability

The purified enzyme and standard isoenzymes were incubated in a water bath at 56° C. for 2, 5, 10, 15 and 20 minutes and at 65° C. for 5 minutes respectively. After heat treatment the samples were chilled immediately in an ice water bath and the remaining alkaline phosphatase activity was assayed.

Inhibition by Amino Acids

In order to define more clearly the isoenzyme, inhibition studies using amino acids were applied to the enzyme samples. The assay was carried out in the presence of L-homoarginine or L-phenylalanine at 5 mM concentration in the reaction mixtures respectively.

Materials

Tris (Trizma Base), 2-amino-2-methyl-1-propanol, beta-napthyl phosphate, Fast Blue BB and neuraminidase (from Clostridia perfringens, Type VI) were obtained from Sigma Chemical Co. St. Louis, Missouri.

Bio Gel-HT and electrophoresis calibration kit for low molecular weight determinations were the products of Nippon Bio-Rad Laboratories, Kita Bldg., 1-3-6 Shiba-Daimon, Minato-ku, Tokyo, 105 Japan.

DEAE Sepharose CL-6B and Sephacryl S-400 were purchased from Pharmacia Fine Chemicals, Piscataway, New Jersey. All other chemicals used were reagent grade and were supplied by Nakarai Chemical Co. Karasuma-Nishiiru Nijo-dori, Nakakyo-ku Kyoto 604 Japan.

The Tris buffer referred to below was 25 mM Tris-HCl (pH 8.00, containing 0.1 mM $MgCl_2$ and 0.01mM $ZnCl_2$.

Enzyme Purification

Step 1: Human Osteosarcoma obtained from nude mice (nu/nu) was frozen at $-70°$ C. until required. A sample (30 g wet weight) was thawed, minced with scissors and homogenized with cold 80 ml of Tris buffer in a Potter-Elvenjem Teflon/glass homogenizer. n-butanol cooled to $-20°$ C. was added until a concentration of 20% (v/v) was reached while the mixture was stirred for 60 minutes. The mixture was then centrifuged at $5,000 \times g$ for 20 minutes with a Hitachi 65P centrifuge using RP 30 rotor to obtain the aqueous phase. Cold acetone at $-20°$ C. was slowly added to the aqueous solution was constant stirring to give a final concentration of 67% (v/v) acetone. The resulting precipitate was allowed to settle for 60 minutes. After centrifugation at $1,500 \times g$ for 15 minutes, the precipitate was recovered and suspended in 20 ml of Tris buffer and dialysed against several changes of this buffer to remove acetone.

Step 2: Saturated ammonium sulfate in Tris buffer was slowly added to the dialysed material from the first step to give a final concentration of 33% (v/v) ammonium sulfate. After 3 hours, inactive precipitate was removed by centrifugation at $3,000 \times g$ for 20 minutes. The supernatant phase was slowly brought to 71% (v/v) ammonium sulfate and allowed to stand for 3 additional hours and then spun at $3,000 \times g$ for 20 minutes. The resultant supernatant was discarded and the solid residue were re-dissolved in 10 mM phosphate buffer (pH 7.6)/0.1 mM $MgCl_2$/0.01 mM $ZnCl_2$ and dialysed against this buffer.

Step 3: The resolubilized material from the second step was applied to a column (2.5 cm diam. $\times$ 8 cm long) of Bio gel-HT equilibrated with 10 mM phosphate buffer (pH 7.6)0.1 mM $MgCl_2$/0.01 mM $ZnCl_2$. The column was washed with 2 column volumes of equilibrating buffer and eluted in a stepwise manner with 150 ml of 500 mM phosphate buffer (pH 7.6)/0.1 mM $MgCl_2$/0.01 mM $ZnCl_2$ (FIG. 1).

Step 4: The active fractions were collected and dialysed against Tris buffer. The material was applied to a DEAE Sepharose CL-6B column (2.5 cm diam. $\times$ 8 cm long) equilibrated with Tris Buffer and eluted with 320 ml Tris buffer that contained NaCl in a linear gradient 0 to 0.4M at a flow rate of 25 ml/h. (FIG. 2).

Step 5: Fractions corresponding to the activity peak eluted at about 0.15M NaCl were pooled and dialysed against a solution of $NH_4OH$ (pH 8.00)/0.1 mM $McCl_2$/0.01 mM $ZnCl_2$. The material was lyophilysed and dissolved in Tris buffer, containing 0.1M NaCl. (FIG. 3).

Step 6: The active fractions from the Sephacryl S-400 were concentrated in the same manner as for Step 5 and rechromatographed on the same column (FIG. 4).

Purification Yield and Purity

A summary of a typical purification is presented in Table 4. The recovered enzyme represented 11% of the original activity of 1520 units/mg of protein. An approximately 900 fold purification from the crude enzyme was achieved. FIGS. 1–4 show the elution profiles from Bio Gel-HT, DEAE Sepharose CL-6b, Sephacryl S-400 and rechromatographed Sephacryl S-400 columns respectively. The purified enzyme was stable at $-20°$ C. in Tris buffer for up to 1 year. Polyacrylamide gel electrophoresis of the final purified enzyme revealed a single protein band which was active on beta-naphthyl phosphate (FIG. 5).

Thin-layer Electrophoresis on Polyacrylamide Gel and Determination of Subunit Molecular Weight Electrophoretic mobility of the purified enzyme on thin-layer polyacrylamide gel was identical to that of bone isoenzyme (FIG. 6). Cathodal change of electrophoretic mobility after neuraminidase treatment indicates that purified enzyme has carbohydrate side chains (FIG. 6).

SDS polyacrylamide gel electrophoresis of the final purified enzyme showed a single protein band, which was estimated to be approximately 80,000 molecular weight (FIG. 7). This molecular weight is consistent with that reported for bovine bone alkaline phosphatase (Hsu, H. T., et al. (1985) J. Biol. Chem. 260:1826).

Treatment with Heat and Inhibitors

The results are summarized in FIG. 8 and Table 5. Based on the sensitivity to heat inactivation and inhibitions by L-homoarginine and L-phenylalanine, the properties of alkaline phosphatase from human osteosarcoma are consistent with those of the bone isoenzyme. It is generally considered in the art that the ALP from normal bone and osteosarcoma are probably identical.

Monoclonal antibodies possess the ability to react with bone ALP on a specific basis, i.e. they recognize the individual molecular configuration and structural conformation of that particular enzyme. Such specificity does not exist with the interaction between wheat germ lectin and the sugar residues of bone ALP since other proteins in the serum may contain identical sugars. Thus other molecules in the serum would have the potential to interfere with the interaction between wheat germ and bone ALP.

Preparation of monoclonal antibodies against human and Rat bone alkaline Phosphatase.

There is theoretically a limitless supply of specific monoclonal antibody reagent which can be produced in ascites form in large amounts using established technology.

Our laboratory has developed monoclonal antibodies against purified bone ALP which react selectively with bone ALP versus liver ALP. Furthermore, these monoclonal antibodies can discriminate between the ALPases of bone, cartilage, kidney and liver (tables 1–3).

The hybridoma cell lines were developed by methods known in the art for monoclonal antibody production [Köhler, G. and Milstein, C. Nature 256:497 (1975)]. Thus splenic lymphocytes derived from mice immunized with Sepharose 6B-purified human bone ALP were fused with mouse plasmacytoma cells (line $\times$ 63 —Ag—8.653) using standard hybridoma technology.

See Oppliger, I. et al. (1986) Bone 7:373 which describes the techniques as follows:

Immunization and cell fusion

Female Balb/c mice were immunized by subcutaneous injection with 35 ug (u=micro) (total protein) of purified human bone ALP (see above) emulsified in complete Freund's adjuvant. Two boosting immunizations in incomplete Freund's adjuvant were given at 2-week intervals. Sera from immunized mice were screened for the presence of specific antibody, using double-diffusion immunoprecipitation [Ouchterlony, (1958) Progr. Allergy 5:1]with staining for ALP activity using alpha-naphthylphosphate as a substrate and Fast Red TR as a coupling agent [Pearse, (1960) Histochemistry, Little Brown & Co., Boston pp. 406–409]and an enzymatic immunosorbent assay as described. The mouse exhibiting the highest serum antibody titer was sacrificed, and the spleen of this animal was removed aseptically. Spleen cells were obtained by teasing the spleen apart with sterile forceps and passing the fragments through a stainless steel mesh. Fusion of splenic lymphocytes with cells of the 8-azaguanine-resistant mouse plasmacytoma cell line X63-Ag-8.653 was performed using a modification of the technique developed by Köhler and Milstein (1975) Supra. Briefly, spleen cells were mixed with plasmacytoma cells at a ratio of 1:7 and centrifuged, and the cell pellet was suspended in 1 ml 40% polyethylene glycol (J. T. Baker Chemical Co., Phillipsburg, NJ), pH 8, over 1 min. Cells were carefully diluted, washed, resuspended in culture medium, and dispersed into 96-well microtiter trays. The cells were maintained in selective medium containing hypoxanthine/aminopeterin/thymidine and examined for the presence of clones. Culture medium from clone-containing wells was assayed for specific antibody production using the enzymatic immunosorbent assay described below. Hybridoma from positive testing wells were subcloned, expanded, and retested. Resulting hybridomas producing antibody were injected intraperitoneally into pristane-primed mice, and antibody-containing ascites fluid was harvested at approximately 2-week intervals.

Preparation of Human Osteosarcoma Alkaline Phosphatase for Elisa Testing

Human osteosarcoma cells (Saos-2 cell line) were grown to confluence as monolayers, washed with phosphate-buffered saline (PBS) buffer (pH 7.4), scraped from the tissue culture flask by a rubber scraper, resuspended at $50 \times 10^6$ cells per ml of PBS and sonicated. Alkaline phosphatase was extracted into N-butanol (20% by volume) at 4° C. for 30 to 60 minutes with one additional sonication. Insoluble debris was removed by centrifugation at 5,000 RPM for 10 minutes, and the ALP-containing supernatant was dialyzed against neutral tris-buffered saline (TBS) containing 0.5% tween-20, to remove butanol. At this point the dialyzed, soluble ALP was ready to ELISA testing.

Human primary osteosarcoma ALP was prepared in a semipure form, using procedures described in the reference of Masuhara, et al. (Bone and Mineral (1987) 3:159–170) through DEAE-sepharose CL-6B chromatography (Step 4).

Preparation of Human Liver and Rat Kidney Alkaline Phosphatase for Elisa Testing Fresh or frozen human liver (obtained at autopsy) or rat kidney was minced into small pieces in PBS buffer (50 g tissue/1,000 ml PBS) and sonicated for two minutes. Alkaline phosphatase was extracted into chilled N-butanol (25% by volume) at 4° C. with sonication, as above, and the insoluble cellular debris was removed by centrifugation at 5,000 RPM for 10 minutes. Protein in the supernatant is precipitated by addition of acetone (2:1 by volume) at 4° C. for 60 minutes, sedimented at 3,000 RPM for 10 minutes, resuspended in TBS, dialyzed against TBS to remove residual acetone and re-precipitated with increasingly concentrated $NH_4SO_4$ (from 30% to 7.1%). The $NH_4SO_4$ precipitate was resuspended in TBS, dialyzed against TBS to remove residual $NH_4SO_4$, chromatographed on a concanavalin-A column, eluted by step-wise addition of 0.1M alpha methyl-D mannoside, dialyzed with TBS, rechromatographed on DEAE-sepharose-CL-6B, eluted by a linear gradient of 0–0.4M NaCl in TBS. The eluted fraction containing most ALP was dialyzed again against TBS, and then used for ELISA testing.

Screening procedure

Affinity purified rabbit antimouse immunoglobulin was adsorbed to flat-bottom microtiter plates (Flow Laboratories, Mclean, Va.) by overnight incubation at room temperature at a concentration of 10 ug/ml in bicarbonate buffer, pH 9.8. The plates were washed thoroughly with 0.05M TBS, pH 8, containing 1% Tween 20 (polyoxyethylene sorbital monolaureate) (TBS-TWEEN). Then 100 ul of hyperimmune serum or hybridoma culture fluid was added to each well and incubated 1 h at 37° C., followed by thorough washing in TBS-Tween buffer. ALP was diluted 1:3 in TBS-Tween buffer, and 100 ul of diluted ALP extract was added to each well, with incubation for 3h at 37° C. After incubation, antigen-containing extract was recovered from the wells for reuse in subsequent assays. The wells were again washed with TBS-Tween, 100 ul of p-nitrophenyl phosphate, 1 mg/ml in bicarbonate buffer, pH 9.8, was added to each well. An increase in reactivity with color yield in this ELISA assay could be obtained when the reaction incubation was done at 50° C. for 10 min.

The $OD_{405}$ was determined by a Multiscan apparatus (Flow Laboratories) at 1 h, 2 h, and after overnight incubation at 37° C. Controls included a sequence of wells in which a single step was omitted to exclude background absorbance and nonspecific binding, as well as a sequence of wells in which normal mouse serum was substituted for hyperimmune serum in the experimental system.

Screening assays to evaluate possible cross-reactivity of the antibody with a variety of ALPase isoenzymes were also performed. (See Oppliger, et al. Bone (1986) 7:373–378). In these assays, commercially prepared (Sigma Chemical Co, St. Louis, Mo.) bovine intestinal (Sigma VII-S), kidney (Sigma XXXI), liver (Sigma IX), and placental (Sigma XV) ALPases, as well as ALP isolated from fetal calf chondrocyte and rachitic rat MV ALP were substituted for fetal calf MV ALP in the same assay system. Enzyme activity of each preparation was determined by measuring the release of p-nitrophenol from p-nitrophenyl phosphate at ambient temperature in a Gilford recording spectrophotometer. The assay mixture (0.5 ml) contained 0.3M 2-amino-2-methyl-1-propanol, pH 10.2, 4 mM p-nitrophenylphosphate, 20 uM $MgCl_2$, and 10 ul of diluted enzyme. The formation of p-nitrophenol was determined spectrophotometrically at 410 nm, and dilutions of each preparation in TBS-Tween were prepared so that 0.033 enzyme units per 100 ul were added to each microtiter well.

Immunoprecipitation procedure

A double-immunosorbent assay for monoclonal antibody against ALP was devised similar to one recently reported by Meyer et al. (1982) Clin. Chem. Acta. 126:109–117.

The cross-reactivity of the ALP described above with the monoclonal anticartilage ALPase could also be determined by double immunoprecipitation. Aliquots of 25 ul of various ALP preparations were added to 150 ul of 2% Tween, 10 mM tris, pH 7.6. A one-fourth dilution of monoclonal antibody was made, and 10 ul was added to each reaction tube and incubated for 1 h to 37° C. This was followed by the addition of 25 ul aliquots of goat anti-mouse IgG. The incubation was continued for another hour at 4° C. A small aliquot (10 ul) was removed for determination of total activity before centrifugation at 9000 RPM for 5 min. Supernatants after the centrifugation were collected and checked for residual enzyme activity. The enzyme bound to monoclonal antibody was calculated from the ratio of enzyme activity in the supernatants (unbound) to the total activity prior to centrifugation.

Hybridoma Cell Lines

The following monoclonal antibody producing cell lines were established:

A. Hybridomas raised against human osteosarcoma ALP: (see table 1)
 1B12—reacts completely with human osteosarcoma, liver and kidney ALP. 1B12 is useful as a control for a positive ALP identification from bone, liver cartilage and kidney. It does not react at all with rat bone, liver or kidney ALP.
 1B3.7, 1E11.3 and 1E11.4 react preferentially with human osteosarcoma versus human liver.
 1E4.1, 2D8.2, and 1A7.1 react exclusively with human bone ALP and not significantly with human kidney.

B. Hybridomas raised against rat cartilage ALP: (see table 3)
 1E10.1 and 1E10.2 react exclusively with rat cartilage and human bone (osteosarcoma) ALP and not significantly with human liver ALP or rat bone ALP (See table 3).
 1B11.1 and 1B11.3 react exclusively with rat cartilage ALP but not with rat bone ALP (Table 3).
 2D11.2 reacts preferentially with rat bone (osteosarcoma) ALP and less avidly with rat cartilage, kidney liver and human bone ALP (Table 3).
 2B11.1 reacts strongly with rat cartilage, bone, liver and kidney ALP, but not with human bone, liver or kidney (Table 3).

Monoclonal antibodies for bone ALP can be linked to tiny sephadex beads for clinical testing. Such linking can be done by methods known in the art. Incubation of such beads with serum or plasma will permit all bone ALP to be selectively affixed to the antibody-coated beads. Mild centrifugation will precipitate the beads, remove the bone ALP quantitatively from solution, and leave only liver ALP in solution for measurement. Alternatively the antibody-coated beads can be encased in a flow-through column in which bone ALP will be selectively retained during the passage of diluted serum or plasma through the column. Liver ALP then can be measured in the effluent.

For direct testing of bone ALP, the affixed bone ALP can be released in an active state from the antibody-coated beads of such a column by a method of elution using a high pH detergent buffer already developed and described by our lab [Hsu, H. T., et al. (1985) J. Biol. Chem. 260:1826], and its activity measured.

An even simpler method for diagnostic testing by a bone-specific anti-ALP antibody makes use of enzyme-linked immunosorbent assay (ELISA) methods already in common usage. By this method, the specific anti-ALP antibody or active fragments thereof as for example the FAB fragment is affixed to the plastic of a microtiter plate well. Any bone alkaline phosphatase available in serum will selectively adhere to the fixed antibody. After washing away extraneous proteins, the presence and amount of adherent bone ALP can be detected by a simple color reaction using p-nitro phenyl phosphate reagent, and quantified by spectrophotometric reading of the microtiter plate in an automatic microtiter plate reader.

One of the preferentially reacting monoclonal antibodies of the invention, 1B3.7, binds bone ALP about two-three times as avidly as liver ALP, but there remains a small binding to the liver isoenzyme. However Table 3 shows monoclonal antibody, 1E10.1, binding human bone ALP exclusively and not human liver significantly. Thus several hybridomas have been established producing monoclonal antibodies that react specifically with bone and show no reaction with kidney ALP and little or no reaction with liver ALP. Monoclonal antibodies 1B12, 1B3.7 and 2B11 are subtyped as IgG gamma(1) and 1E10.1 is IgG gamma (2B).

It will be understood that the specification and examples serve as illustrations of the present invention but are not limitative thereof and that other embodiments within the spirit and scope of the invention will suggest themselves to those skilled in the art.

In addition, we report a monoclonal antibody against rat chondrocyte cartilage which however is negative against rat bone tissue (UMR).

Both the bone and kidney isoenzymes are believed to contain the same protein core structure. Therefore, antibody discrimination between bone and kidney ALPs is probably possible on the basis of selective reaction with differing sugar residues in the two molecules.

Development of a lab test to distinguish between bone and liver alkaline phosphatase is now possible. In humans it is often important to diagnose diseases primary to the liver, e.g. hepatitis, cholangititis, cirrhosis, and cancer arising in the liver, all of which cause an elevation of the serum alkaline phosphatase. These diseases must be distinguished from diseases arising in the bone which cause elevated serum alkaline phosphatase, e.g. Paget's disease of bone, certain cancers metastatic to bone especially prostate cancer, primary bone cancer (osteosarcoma), fractures with or without metastatic cancer pre-disposing to fracturing, and metabolic bone diseases which cause elevated bone alkaline phosphatase such as hyperparathyroidism and the osteodystrophy of renal failure.

The most important clinical distinction in today's medical practice is between ALP of liver origin and ALP of bone origin, however, as indicated in the support data above, some of the monoclonal antibodies we have developed also can distinguish the alkaline phosphatase of bone from that of kidney or even of cartilage origin. It is likely that diseases of kidney or cartilage will need to be diagnosed and distinguished from diseases primary to bone.

The invention can be applied in veterinary medicine. In older animals, particularly horses, dogs and cats, serum ALP rises, and the cause is often undetermined. This may be due to the presence of chronic active and/or persistent hepatitis, diagnoses that could be assuredly confirmed if the presence of circulating liver ALP could be established. Horses often have liver disease caused by parasites or from eating toxic alkaloids in forage grass, and the liver as a primary site of these diseases can be confirmed. Another important cause of elevated serum ALP of bone origin in horses, is caused by training stress and over-exercise. Having a simple, bone-specific alkaline phosphatase test would indicate the presence and severity of training stress, and could be used to monitor clinical improvement with rest, or to avoid development of training stress in the first place. Another possible use would be in the diagnosis of bone cancer (osteosarcoma) which occurs rather frequently in the distal fore-leg of large breed dogs. Such malignant bone tumors are often difficult to diagnose by x-ray but are known to produce significant elevations of bone-type alkaline phosphatase in the serum.

Diagnostic imaging of bone tumors or localized areas of fracture or increased bone metabolism (as in Paget's disease) can be accomplished if anti-bone ALP or functional subunits of the antibody could be coupled with a radio-active tag. Upon injection of tagged antibody into the patient or animal, the antibody would target and/or accumulate at sites of elevated ALP synthesis, storage and/or release and could be used for radionuclide imaging. An antibody to bone ALP could be coupled with a tumoricidal agent by methods known in the art for in vivo chemotherapeutic homing in and other bone cancers. Bone specific monoclonal antibodies also can be used for microscopic localization of cells producing excessive ALP, the cells of primary bone tumors, granulocytic leukemia, or metastatic tumors from bone in which the lack of cellular differentiation prevents an accurate determination of the tumor's origination in bone.

Diagnostic imaging of bone tumors or localized areas of fracture or increased bone metabolism (as in Paget's disease) might be accomplished if anti-bone ALP or functional subunits of the antibody could be conjugated with a radioactive tag such as $^{131}$Iodine or $^{111}$Indium. Such diagnostic reagents have been reported successful for radionuclide imaging of human osteosarcomas (Armitage, et al., (1986) Cancer 58:37-42) using a monoclonal antibody raised against a human osteosarcoma cell line (791 T/36) whole cell antigen. In this study which showed improved imaging over the conventional TC99-diphosphonate method, the monoclonal antibody was not specific for bone but also cross-reacted against colon, lung, prostate and cervical (HeLa) carcinoma cells. A bone specific anti-ALP such as described here would possess greater utility for such targeting. Upon injection of tagged ALP antibody into the patient or animal, the antibody should accumulate at sites of elevated ALP synthesis, storage and/or release and could be used for radionuclide imaging.

An antibody to bone ALP might also be conjugated with a tumoricidal agent for in vivo chemotherapeutic homing in bone cancers. Targeted monoclonal antibodies carrying cytotoxic agents such as ricin A-chain, pseudomonas exotoxin-A or methotrexate or 131Iodine are being actively investigated for treatment of malignant lymphoma (Bregni et al., (1986) Cancer Res. 46:1208-1213), breast cancer (Bjorn, M.J., (1986) Cancer Res. 46:3262-3267), colorectal cancer, (Oldham, R. K. (1984) Med. Oncol. Tumor Pharmacother. 1:51-62) and other types.

Bone specific monoclonal antibodies also could be used for microscopic immunolocalization of cells producing excessive ALP, such as the cells of primary bone tumors, granulocytic leukemia, or metastatic tumors from bone.

The hybridoma cell lines of the invention are on deposit at the University of Kansas ("UKAN") Medical Center, School of Medicine, Department of Pathology and Oncology 39th and Rainbow Blvd., Kansas City, Kansas 66103 under the following designations (UKAN) and 1E10.1, 2B11.1 and 1B12 are also on deposit at the American Type Culture ("ATCC") 12301 Parklawn Drive, Rockville, Md. 20852-1776 collections as of Feb. 3, 1988 under the following designations (ATCC):

| UKAN | ATCC |
|---|---|
| 1E10.1 | |
| 1E10.2 | |
| 1B11.1 | |
| 1B11.3 | |
| 1B12 | |
| 2D11.2 | |
| 2B11.1 | |
| 1B3.7 | |
| 1E11.3 | |
| 1E11.4 | |
| 1E4.1 | |
| 2D8.2 | |
| 1A7.1 | |

2B11.1 may be on deposit at the ATCC as 2B11.

The deposited monoclonal antibodies have the following UKAN and ATCC designations:

| UKAN | ATCC |
|---|---|
| 1E10.1 | 9660 |
| 2B11 (or 2B11.1) | 9638 |
| 1B12 | 9637 |

TABLE 1

Monoclonal antibodies against human osteosarcoma ALP. Some show selective reactivity for human bone ALP versus human liver ALP.

| mAb | BONE ALP | LIVER ALP |
|---|---|---|
| 1B12 | .688 | .687 |
| 1B3.7 | .516 | .398 |
| 1E11.3 | .301 | .138 |
| 1E11.4 | .284 | .113 |

TABLE 2

Monoclonal antibodies against human osteosarcoma ALP. Some show exclusive reactivity for human bone ALP versus human kidney ALP.

| mAb | BONE ALP | KIDNEY ALP |
|---|---|---|
| 1B12 | .868 | .666 |
| 1E4.1 | .364 | .080 |
| 2D8.2 | .338 | .030 |
| 1A7.1 | .308 | .064 |

TABLE 2-continued

Monoclonal antibodies against human osteosarcoma ALP.
Some show exclusive reactivity for human bone ALP
versus human kidney ALP.

| mAb | BONE ALP | KIDNEY ALP |
|---|---|---|
| 1B3.7 | .516 | .265 |

TABLE 3

REACTIVITY OF MONOCLONAL ANTIBODIES
TO ALKALINE PHOSPHATASE

| Monoclonal Antibody | Rat Cartilage ALP | Rat Osteosarcoma ALP | Rat Liver ALP | Rat Kidney ALP | Human Osteosarcoma ALP | Human Liver ALP |
|---|---|---|---|---|---|---|
| 1E10.1 | .207 | .020 | .011 | .020 | .139 | .007 |
| 1E10.2 | .282 | .008 | .001 | .020 | | |
| 1B11.1* | .052 | .007 | .000 | .026 | | |
| 1B11.3* | .248 | .008 | .004 | .023 | | |
| 2D11.2 | .183 | .328 | .118 | .105 | .041 | .003 |
| 2B11.1 | .279 | .262 | .247 | .239 | .052 | .005 |

*grows slowly

Table shows cross-reactivity of mAbs raised against rat cartilage which react exclusively with human bone versus human liver (1E10.1) and also discrimate rat cartilage ALP from the ALPs of rat osteosarcoma, kidney and liver.

TABLE 4

PURIFICATION OF ALKALINE PHOSPHATASE
FROM HUMAN OSTEOSARCOMA

| STEP | Total Protein (mg) | Total Activity (units) | Specific Activity (units/mg) | Yield (%) | Purification |
|---|---|---|---|---|---|
| Crude homogenate | 5100 | 8670 | 1.7 | 100 | 1 |
| n-Butanol extract | 625 | 6938 | 11.1 | 80 | 6.5 |
| Ammonium sulfate fractionation (33%-70%) | 273 | 5597 | 20.5 | 65 | 12 |
| Bio-Gel HT | 178 | 5299 | 29.8 | 61 | 18 |
| DEAE Sepharose CL-6B | 20 | 3000 | 150 | 35 | 88 |
| Sephacryl S-400 | 1.8 | 1391 | 773 | 16 | 455 |
| Sephacryl S-400 (rachromatography) | 0.6 | 912 | 1520 | 11 | 894 |

TABLE 5

EFFECT OF HEAT AND AMINO ACIDS
ON ALKALINE PHOSPHATASE
FROM HUMAN OSTEOSARCOMA

| | Inhibition (%) |
|---|---|
| 56° C., 15 min. | 90 |
| 65° C., 5 min. | 100 |
| L-phenylalanine | 5 |
| L-homoarginine | 64 |

What is claimed:

1. A monoclonal antibody capable of immunologically distinguishing between different human tissue isoenzymes of alkaline phosphatase wherein said monoclonal antibody is 1E10.1 which specifically binds to human bone alkaline phosphatase but does not bind to human liver alkaline phosphatase and is produced by the hybridoma having ATCC accession number HB 9660.

2. Hybridoma cell line producing monoclonal antibody 1E10.1 which immunologically distinguishes between different human tissue isoenzymes of alkaline phosphatase in specifically binding to human bone alkaline phosphatase but not to human liver alkaline phosphatase.

3. The monoclonal antibody of claim 1 wherein the bone alkaline phosphatase is osteosarcoma alkaline phosphatase.

4. Monoclonal antibody 2B11.1 which immunologically binds to rat bone, rat cartilage, rat liver and rat kidney alkaline phosphatase isoenzymes and is produced by the hybridoma having ATCC accession number HB 9638.

5. Hybridoma cell line ATCC HB 9638 producing monoclonal antibody 2B11.1 which immunologically binds to rat bone, rat cartilage, rat liver, and rat kidney alkaline phosphatase isoenzymes.

6. A kit for detecting the presence of human bone alkaline phosphatase in the presence of human liver alkaline phosphatase comprising
monoclonal antibodies 1E10.1 and 2B11.1 wherein monoclonal antibody 1E10.1 specifically binds to human bone alkaline phosphatase but does not bind to human liver alkaline phosphatase and monoclonal antibody 2B11.1 serves as a negative control reagent.

7. A monoclonal antibody which immunologically distinguishes between different human tissue isoenzymes of alkaline phosphatase wherein said monoclonal antibody is 1E10.1 which specifically binds to human bone alkaline phosphatase and does not bind to human liver alkaline phosphatase said monoclonal antibody being produced by hybridoma cell line HB 9660 resulting from an immunization with rat cartilage alkaline phosphatase antigen.

* * * * *

UNITED STATES PATENT AND TRADEMARK OFFICE
CERTIFICATE OF CORRECTION

PATENT NO. : 5,087,573
DATED : February 11, 1992
INVENTOR(S) : H. Clarke Anderson, et al.

It is certified that error appears in the above-identified patent and that said Letters Patent is hereby corrected as shown below:

| | |
|---|---|
| Col. 11, line 40: | after "specific" insert -- monoclonal --. |
| Col. 11, line 41: | after "microscopic" delete "ocalization" and insert -- immunolocalization --. |
| Col. 11, line 42: | after "excessive" delete "ALF" and insert -- ALP, such as --. |
| Col. 11, line 43: | after "granulocytic" delete "mia" and insert -- leukemia --. |
| Col. 14, line 19 (Claim 2): | after "line" insert -- HB 9660 --. |
| Abstract, line 4: | change "binding" to -- bonding --. |

Signed and Sealed this

Sixteenth Day of November, 1993

Attest:

BRUCE LEHMAN

*Attesting Officer*  *Commissioner of Patents and Trademarks*